(12) United States Patent
Garcia et al.

(10) Patent No.: US 8,299,213 B2
(45) Date of Patent: Oct. 30, 2012

(54) SYNTHETIC OR NATURAL PEPTIDES BINDING PROTEIN PHOSPHATASE 2A, IDENTIFICATION METHOD AND USES

(75) Inventors: Alphonse Garcia, Montrouge (FR); Xavier Cayla, Rochecorbon (FR); Angelita Rebollo, Madrid (ES); Gordon Langsley, Paris (FR)

(73) Assignee: Universite Pierre et Marie Curie (Paris 6), Paris (FR)

( * ) Notice: Subject to any disclaimer, the term of this patent is extended or adjusted under 35 U.S.C. 154(b) by 0 days.

(21) Appl. No.: 13/040,862

(22) Filed: Mar. 4, 2011

(65) Prior Publication Data
US 2011/0269674 A1    Nov. 3, 2011

Related U.S. Application Data

(60) Division of application No. 10/763,286, filed on Jan. 26, 2004, now abandoned, which is a continuation of application No. PCT/FR02/02705, filed on Jul. 26, 2002.

(30) Foreign Application Priority Data

Jul. 27, 2001    (FR) ...................... 01 10139

(51) Int. Cl.
| | |
|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. ...................................... 530/327
(58) Field of Classification Search .................. None
See application file for complete search history.

(56) References Cited

U.S. PATENT DOCUMENTS

| | | | |
|---|---|---|---|
| 7,056,735 B2 | 6/2006 | Jacotot et al. | |
| 2003/0077826 A1 | 4/2003 | Edelman et al. | |

FOREIGN PATENT DOCUMENTS

| | | |
|---|---|---|
| WO | WO 98/01563 | 1/1998 |
| WO | WO 01/04629 A1 | 1/2001 |
| WO | WO 01/32867 | 5/2001 |
| WO | WO 01/90159 A2 | 11/2001 |

OTHER PUBLICATIONS

Sarno et al. Polyamines as negative regulators of casein kinase-2: the phosphorylation of calmodulin triggered by polylysine and by the alpha[66-86] peptide is prevented by spermine. Biochem Biophys Res Commun, 1993, 194(1), pp. 83-90.*
Zaremberg et al. Mechanism of Activation of cAMP-Dependent Protein Kinase: In Mucor rouxii the Apparent Specific Activity of the cAMP-Activated Holoenzyme is Different than That of Its Free Catalytic Subunit. Archives of Biochemistry and Biophysics. vol. 381. No. 1, 2000. pp. 74-82.*

Meggio et al. Casein Kinase 2 Down-Regulation and Activation by Polybasic Peptides Are Mediated by Acidic Residues in the 55-64 Region of the beta-Subuint. A Study with Calmodulin As Phosphoryatable Substrate. Biochemistry, 1994, vol. 33, pp. 4336-4342.*
H.J.C. Berendsen. A Glimpse of the Holy Grail? Science (1998) 282, pp. 642-643.*
Rudinger. In: Peptide Hormones, JA Parsons, Ed. (1976) 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Champe et al. Biochemistry, 2nd Edition, Lippincott's Illustrated Reviews. 1994, pp. 13-14, 343-344.*
Elgert. Immunology: Understanding the Immune System, Chapter 4: Antibody structure and function. 1998. John Wiley & Sons, Inc., pp. 58-78.*
Coin et al. Solid-phase peptide synthesis: from standard procedures to the synthesis of difficult sequences. Nature Protocols. 2007. vol. 2, No. 12, pp. 3247-3256.*
Hruby. Designing Peptide Receptor Agonists and Antagonists. Nature Reviews. Drug Discovery. vol. 1, Nov. 2002, pp. 847-858.*
Arunagiri, et al. A C-terminal domain of HIV-1 accessory protein Vpr is involved in penetration, mitochondrial dysfunction and apoptosis of human CD4+ lymphocytes. Apoptosis. 1997, vol. 2, pp. 69-76.
Macreadi et al. A domain of human immunodeficiency virus type 1 Vpr containing repeated H(S/F)RIG amino acid motifs causes cell growth arrest and structural defects. PNAS 1995, vol. 92, pp. 2770-2774.
Neil E. Faulkner, et al., "Protein Phosphatase 2A Activates the HIV-2 Promoter through Enhancer Elements That Include the pets Site", The Journal of Biological Chemistry, vol. 276, No. 28, XP-002201695, Jul. 13, 2001, pp. 25804-25812.
Database EMBL 'Online!, AN P89821, XP-002201698, May 1, 1997.
Database EMBL 'Online!, AN Q9QV79, XP-002201699, May 1, 2000.
Carlos S. Moreno, et al., "WD40 Repeat Proteins Striatin and S/G$_2$ Nuclear Autoantigen Are Members of a Novel Family of Calmodulin-binding Proteins That Associate with Protein Phosphatase 2A", The Journal of Biological Chemistry, vol. 275, No. 8, XP-002201696, Feb. 25, 2000, pp. 5257-5263.
Carlos S. Moreno, et al., "A Mammalian Homolog of Yeast MOB1 Is Both a Member and a Putative Substrate of Striatin Family-Protein Phosphatase 2A Complexes", The Journal of Biological Chemistry, vol. 276, No. 26, XP-002201697, Jun. 29, 2001, pp. 24253-24260.

* cited by examiner

Primary Examiner — Marcela M Cordero Garcia
(74) Attorney, Agent, or Firm — Oblon, Spivak, McClelland, Maier & Neustadt, L.L.P.

(57) ABSTRACT

The present invention relates to novel synthetic or natural peptides for use in treating viral or parasitic infections or in the treatment of tumors. The peptides of the present invention are less than 30 amino acids in size, preferably less than 20 amino acids, in particular 15 to 20 amino acids, and in vitro the peptides specifically bind a type 2A protein phosphatase holoenzyme or one of its subunits. The invention also relates to a method for identifying said peptides, and to their uses.

9 Claims, 6 Drawing Sheets

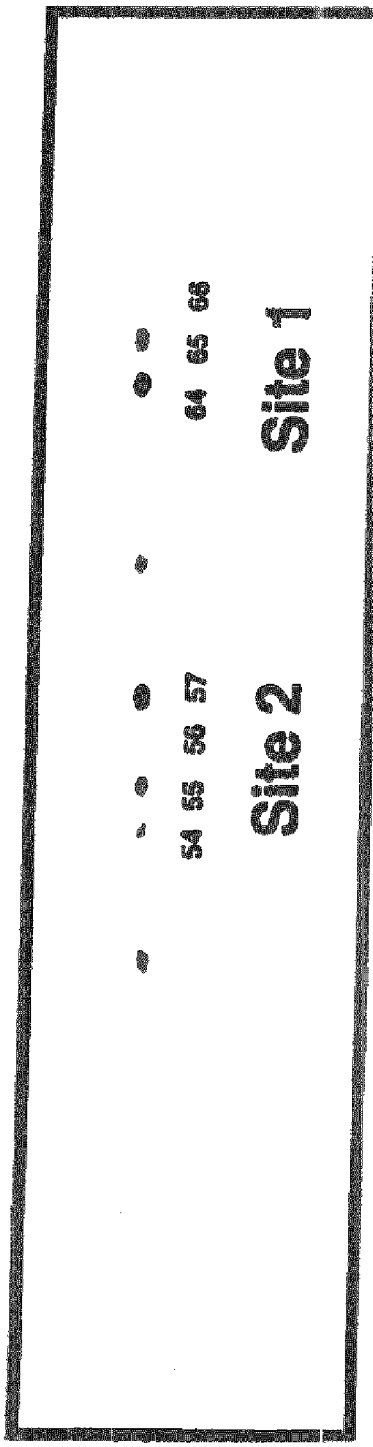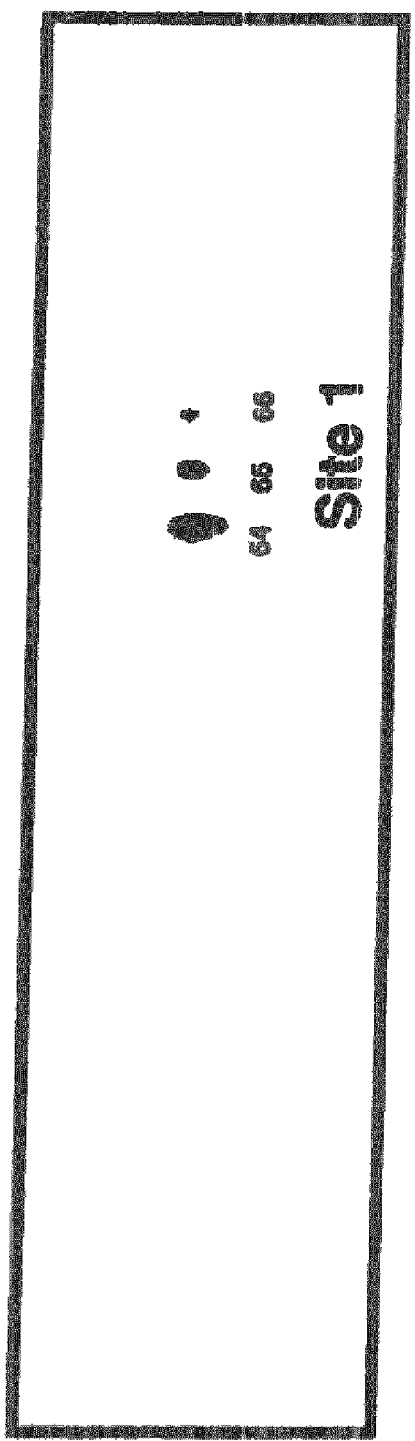

Key: conc fd en uM = fd conc, uM

SEQUENCE LISTING

<160> NUMBER OF SEQ ID NOS: 51

<210> SEQ ID NO 1
<211> LENGTH: 18
<212> TYPE: PRT
<213> ORGANISM: Human immunodeficiency virus

<400> SEQUENCE: 1

Val Glu Ala Leu Ile Arg Ile Leu Gln Gln Leu Leu Phe Ile His Phe
1               5                   10                  15

Arg Ile

<210> SEQ ID NO 2
<211> LENGTH: 16
<212> TYPE: PRT

-continued

<213> ORGANISM: Human immunodeficiency virus

<400> SEQUENCE: 2

Arg His Ser Arg Ile Gly Ile Ile Gln Gln Arg Arg Thr Arg Asn Gly
1               5                   10                  15

<210> SEQ ID NO 3
<211> LENGTH: 14
<212> TYPE: PRT
<213> ORGANISM: Theileria parva

<400> SEQUENCE: 3

Arg Lys Ile Gly Arg Gly Lys Phe Ser Glu Val Phe Glu Gly
1               5                   10

<210> SEQ ID NO 4
<211> LENGTH: 30
<212> TYPE: PRT
<213> ORGANISM: Theileria parva

<400> SEQUENCE: 4

Thr Val Thr Lys Asp Lys Cys Val Ile Lys Ile Leu Lys Pro Val Lys
1               5                   10                  15

Lys Lys Lys Ile Lys Arg Glu Ile Lys Ile Leu Gln Asn Leu
            20                  25                  30

<210> SEQ ID NO 5
<211> LENGTH: 16
<212> TYPE: PRT
<213> ORGANISM: Theileria parva

<400> SEQUENCE: 5

Lys Ile Leu Arg Leu Ile Asp Trp Gly Leu Ala Glu Phe Tyr His Pro
1               5                   10                  15

<210> SEQ ID NO 6
<211> LENGTH: 12
<212> TYPE: PRT
<213> ORGANISM: Human immunodeficiency virus

<400> SEQUENCE: 6

Val Glu Ala Leu Ile Arg Ile Leu Gln Gln Leu Leu
1               5                   10

<210> SEQ ID NO 7
<211> LENGTH: 12
<212> TYPE: PRT
<213> ORGANISM: Human immunodeficiency virus

<400> SEQUENCE: 7

Ala Leu Ile Arg Ile Leu Gln Gln Leu Leu Phe Ile
1               5                   10

<210> SEQ ID NO 8
<211> LENGTH: 12
<212> TYPE: PRT
<213> ORGANISM: Human immunodeficiency virus

<400> SEQUENCE: 8

Ile Arg Ile Leu Gln Gln Leu Leu Phe Ile His Phe
1               5                   10

<210> SEQ ID NO 9
<211> LENGTH: 12
<212> TYPE: PRT

<213> ORGANISM: Human immunodeficiency virus

<400> SEQUENCE: 9

Ile Leu Gln Gln Leu Leu Phe Ile His Phe Arg Ile
1               5                   10

<210> SEQ ID NO 10
<211> LENGTH: 12
<212> TYPE: PRT
<213> ORGANISM: Human immunodeficiency virus

<400> SEQUENCE: 10

Arg His Ser Arg Ile Gly Ile Ile Gln Gln Arg Arg
1               5                   10

<210> SEQ ID NO 11
<211> LENGTH: 12
<212> TYPE: PRT
<213> ORGANISM: Human immunodeficiency virus

<400> SEQUENCE: 11

Ser Arg Ile Gly Ile Ile Gln Gln Arg Arg Thr Arg
1               5                   10

<210> SEQ ID NO 12
<211> LENGTH: 12
<212> TYPE: PRT
<213> ORGANISM: Human immunodeficiency virus

<400> SEQUENCE: 12

Ile Gly Ile Ile Gln Gln Arg Arg Thr Arg Asn Gly
1               5                   10

<210> SEQ ID NO 13
<211> LENGTH: 12
<212> TYPE: PRT
<213> ORGANISM: Theileria parva

<400> SEQUENCE: 13

Thr Val Thr Lys Asp Lys Cys Val Ile Lys Ile Leu
1               5                   10

<210> SEQ ID NO 14
<211> LENGTH: 12
<212> TYPE: PRT
<213> ORGANISM: Theileria parva

<400> SEQUENCE: 14

Thr Lys Asp Lys Cys Val Ile Lys Ile Leu Lys Pro
1               5                   10

<210> SEQ ID NO 15
<211> LENGTH: 12
<212> TYPE: PRT
<213> ORGANISM: Theileria parva

<400> SEQUENCE: 15

Asp Lys Cys Val Ile Lys Ile Leu Lys Pro Val Lys
1               5                   10

<210> SEQ ID NO 16
<211> LENGTH: 12
<212> TYPE: PRT
<213> ORGANISM: Theileria parva

<400> SEQUENCE: 16

```
Cys Val Ile Lys Ile Leu Lys Pro Val Lys Lys Lys
1               5                   10
```

<210> SEQ ID NO 17
<211> LENGTH: 12
<212> TYPE: PRT
<213> ORGANISM: Theileria parva

<400> SEQUENCE: 17

```
Ile Lys Ile Leu Lys Pro Val Lys Lys Lys Lys Ile
1               5                   10
```

<210> SEQ ID NO 18
<211> LENGTH: 12
<212> TYPE: PRT
<213> ORGANISM: Theileria parva

<400> SEQUENCE: 18

```
Ile Leu Lys Pro Val Lys Lys Lys Lys Ile Lys Arg
1               5                   10
```

<210> SEQ ID NO 19
<211> LENGTH: 12
<212> TYPE: PRT
<213> ORGANISM: Theileria parva

<400> SEQUENCE: 19

```
Lys Pro Val Lys Lys Lys Lys Ile Lys Arg Glu Ile
1               5                   10
```

<210> SEQ ID NO 20
<211> LENGTH: 12
<212> TYPE: PRT
<213> ORGANISM: Theileria parva

<400> SEQUENCE: 20

```
Val Lys Lys Lys Lys Ile Lys Arg Glu Ile Lys Ile
1               5                   10
```

<210> SEQ ID NO 21
<211> LENGTH: 12
<212> TYPE: PRT
<213> ORGANISM: Theileria parva

<400> SEQUENCE: 21

```
Lys Lys Lys Ile Lys Arg Glu Ile Lys Ile Leu Gln
1               5                   10
```

<210> SEQ ID NO 22
<211> LENGTH: 12
<212> TYPE: PRT
<213> ORGANISM: Theileria parva

<400> SEQUENCE: 22

```
Lys Ile Lys Arg Glu Ile Lys Ile Leu Gln Asn Leu
1               5                   10
```

<210> SEQ ID NO 23
<211> LENGTH: 12
<212> TYPE: PRT
<213> ORGANISM: Theileria parva

<400> SEQUENCE: 23

```
Lys Ile Leu Arg Leu Ile Asp Trp Gly Leu Ala Glu
1               5                   10
```

<210> SEQ ID NO 24
<211> LENGTH: 12
<212> TYPE: PRT
<213> ORGANISM: Theileria parva

<400> SEQUENCE: 24

Leu Arg Leu Ile Asp Trp Gly Leu Ala Glu Phe Tyr
1               5                   10

<210> SEQ ID NO 25
<211> LENGTH: 12
<212> TYPE: PRT
<213> ORGANISM: Theileria parva

<400> SEQUENCE: 25

Leu Ile Asp Trp Gly Leu Ala Glu Phe Tyr His Pro
1               5                   10

<210> SEQ ID NO 26
<211> LENGTH: 54
<212> TYPE: DNA
<213> ORGANISM: Human immunodeficiency virus

<400> SEQUENCE: 26
gtggaagcct taataagaat tctgcaacaa ctgctgttta ttcatttcag aatt        54

<210> SEQ ID NO 27
<211> LENGTH: 48
<212> TYPE: DNA
<213> ORGANISM: Human immunodeficiency virus

<400> SEQUENCE: 27
cgacatagca gaataggcat tattcaacag aggagaacaa gaaatgga              48

<210> SEQ ID NO 28
<211> LENGTH: 42
<212> TYPE: DNA
<213> ORGANISM: Theileria parva

<400> SEQUENCE: 28
aggaagatcg gaagagggaa gttcagtgaa gtttttgagg ga                    42

<210> SEQ ID NO 29
<211> LENGTH: 90
<212> TYPE: DNA
<213> ORGANISM: Theileria parva

<400> SEQUENCE: 29
acagtaacga aggataaatg cgtaataaaa atcctaaagc ctgtaaagaa gaagaaaatc    60
aagagagaga ttaagattct acagaaccta                                    90

<210> SEQ ID NO 30
<211> LENGTH: 48
<212> TYPE: DNA
<213> ORGANISM: Theileria parva

<400> SEQUENCE: 30
aaaatactaa ggctaattga ctggggatta gctgagtttt accaccca               48

<210> SEQ ID NO 31
<211> LENGTH: 12
<212> TYPE: PRT
<213> ORGANISM: Theileria parva

```
<400> SEQUENCE: 31

Arg Lys Ile Gly Arg Gly Lys Phe Ser Glu Val Phe
1               5                   10

<210> SEQ ID NO 32
<211> LENGTH: 12
<212> TYPE: PRT
<213> ORGANISM: Theileria parva

<400> SEQUENCE: 32

Ile Gly Arg Gly Lys Phe Ser Glu Val Phe Glu Gly
1               5                   10

<210> SEQ ID NO 33
<211> LENGTH: 11
<212> TYPE: PRT
<213> ORGANISM: Theileria parva

<400> SEQUENCE: 33

Pro Arg Arg Pro Gly Pro Thr Arg Lys His Tyr
1               5                   10

<210> SEQ ID NO 34
<211> LENGTH: 18
<212> TYPE: PRT
<213> ORGANISM: Theileria parva

<400> SEQUENCE: 34

Pro Arg Arg Pro Gly Pro Thr Arg Lys Pro Arg Arg Pro Gly Pro Thr
1               5                   10                  15

Arg Lys

<210> SEQ ID NO 35
<211> LENGTH: 18
<212> TYPE: PRT
<213> ORGANISM: Theileria parva

<400> SEQUENCE: 35

Arg Gln Lys Arg Leu Ile Arg Gln Lys Arg Leu Ile Arg Gln Lys Arg
1               5                   10                  15

Leu Ile

<210> SEQ ID NO 36
<211> LENGTH: 6
<212> TYPE: PRT
<213> ORGANISM: Theileria parva

<400> SEQUENCE: 36

Arg His Ser Arg Ile Gly
1               5

<210> SEQ ID NO 37
<211> LENGTH: 12
<212> TYPE: PRT
<213> ORGANISM: Theileria parva

<400> SEQUENCE: 37

Arg His Ser Arg Ile Gly Arg His Ser Arg Ile Gly
1               5                   10

<210> SEQ ID NO 38
<211> LENGTH: 18
<212> TYPE: PRT
```

<213> ORGANISM: Theileria parva

<400> SEQUENCE: 38

Arg His Ser Arg Ile Gly Arg His Ser Arg Ile Gly Arg His Ser Arg
1               5                   10                  15

Ile Gly

<210> SEQ ID NO 39
<211> LENGTH: 18
<212> TYPE: PRT
<213> ORGANISM: Theileria parva

<400> SEQUENCE: 39

Ala His Ser Arg Ile Gly Ala His Ser Arg Ile Gly Ala His Ser Arg
1               5                   10                  15

Ile Gly

<210> SEQ ID NO 40
<211> LENGTH: 16
<212> TYPE: PRT
<213> ORGANISM: Theileria parva

<400> SEQUENCE: 40

Arg His Ser Arg Ile Gly Val Thr Arg Gln Arg Arg Ala Arg Asn Gly
1               5                   10                  15

<210> SEQ ID NO 41
<211> LENGTH: 16
<212> TYPE: PRT
<213> ORGANISM: Theileria parva

<400> SEQUENCE: 41

Arg Arg Arg Arg Arg Arg Arg Ser Arg Gly Arg Arg Arg Arg Thr Tyr
1               5                   10                  15

<210> SEQ ID NO 42
<211> LENGTH: 6
<212> TYPE: PRT
<213> ORGANISM: Theileria parva

<400> SEQUENCE: 42

Arg Gln Lys Arg Leu Ile
1               5

<210> SEQ ID NO 43
<211> LENGTH: 30
<212> TYPE: PRT
<213> ORGANISM: Theileria parva

<400> SEQUENCE: 43

Thr Val Thr Lys Asp Lys Cys Val Ile Lys Ile Leu Lys Pro Val Lys
1               5                   10                  15

Lys Lys Lys Ile Lys Arg Glu Ile Lys Ile Leu Gln Asn Leu
                20                  25                  30

<210> SEQ ID NO 44
<211> LENGTH: 29
<212> TYPE: PRT
<213> ORGANISM: Theileria parva

<400> SEQUENCE: 44

Leu Phe Ile His Phe Arg Ile Gly Cys Gln His Ser Arg Ile Gly Ile
1               5                   10                  15

Thr Arg Arg Arg Arg Val Arg Asp Gly Ser Ser Arg Pro
            20                  25

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Ile Gly Arg
1

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Ile Leu Lys Pro Val Lys Lys Lys Ile Lys Arg Glu Lys Ile
1               5                   10                  15

Leu Gln Asn Leu
            20

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Ile Leu Arg Leu Ile
1               5

<210> SEQ ID NO 48
<211> LENGTH: 7
<212> TYPE: PRT
<213> ORGANISM: Plasmodium falciparum

<400> SEQUENCE: 48

Glu Cys Asn Arg Pro Ala Val
1               5

<210> SEQ ID NO 49
<211> LENGTH: 5
<212> TYPE: PRT
<213> ORGANISM: Bos sp.

<400> SEQUENCE: 49

Asn Asn Glu Val Glu
1               5

<210> SEQ ID NO 50
<211> LENGTH: 8
<212> TYPE: PRT
<213> ORGANISM: Leishmania sp.

<400> SEQUENCE: 50

Asn Asn Glu Lys Val Val Val Glu
1               5

```
<210> SEQ ID NO 51
<211> LENGTH: 10
<212> TYPE: PRT
<213> ORGANISM: Leishmania sp.

<400> SEQUENCE: 51

Lys Val Leu Arg Gln Val Leu Met Val Thr
1               5                   10
```

SYNTHETIC OR NATURAL PEPTIDES BINDING PROTEIN PHOSPHATASE 2A, IDENTIFICATION METHOD AND USES

CROSS-REFERENCE TO RELATED APPLICATIONS

The present application is a divisional of U.S. patent application Ser. No. 10/763,286, filed on Jan. 26, 2004, now abandoned which is a continuation of International patent application PCT/FR02/02705, filed on Jul. 26, 2002, which claims priority to French patent application 01/10139, filed on Jul. 27, 2001.

FIELD OF THE INVENTION

The invention relates to novel synthetic or natural peptides, in particular for use in treating viral or parasitic infections or in the treatment of tumors, said peptides being less than 30 amino acids in size, preferably less than 20 amino acids, in particular 15 to 20 amino acids, and characterized in that in vitro, they specifically bind a type 2A protein phosphatase holoenzyme or one of its subunits. The invention also relates to a method for identifying said peptides, and to their uses.

DISCUSSION OF THE BACKGROUND

Given the role of the peptides of the invention in modulating the activity of cellular protein phosphatase 2A, it is important in the introduction to recall the current knowledge regarding protein phosphatase 2As, their physiological role and their interactions with certain cellular, viral or parasitic proteins.

Cell physiology is partially controlled by modulating protein phosphorylation. The phosphorylation state of cell proteins depends on the antagonist action of protein kinases which phosphorylates them and protein phosphatases which dephosphorylate them.

Protein phosphatases are divided into two principal groups: tyrosine phosphatases and serine/threonine phosphatases. Serine/threonine phosphatases are classified into two categories which depend on the specificity of their substrate and their sensitivity to certain inhibitors, namely type 1 phosphatases (PP1) and type 2 phosphatases (PP2). Type 2 phosphatases are themselves divided into different classes, including phosphatase 2A (PP2A), phosphatase 2B or calcineurine the activity of which is regulated by calcium, and phosphatase 2C (PP2C) the activity of which is regulated by magnesium.

It is now known that type 2A phosphatases are highly conserved during evolution and are potentially involved in regulating many biological processes. PP2A enzymes have been clearly involved in regulating transcription, control of the cell cycle or viral transformation. Further, PP2As are targeted by different viral or parasitic proteins, suggesting a role for PP2As in host-pathogen interactions.

PP2As are oligomeric complexes (holoenzymes) each comprising a catalytic subunit (C) and one or two regulating subunits (A) and (B). The structure of subunit (A) consists of 15 imperfect repeats of a conserved amino acid sequence of 38 to 40 amino acids, certain of which interact with subunits (B) and (C). Subunits (A) and (C), conserved during evolution, constitute the base structure of the enzyme and are expressed constitutively. In contrast, subunits (B) constitute a family of regulating proteins not connected via a common structure and expressed differentially (Cohen P. The structure and regulation of protein phosphatases. *Annu Rev Biochem* 1989; 58: 453-508). Protein phosphatase 2As exist in vivo in two classes with different forms: a dimeric form (AC) and a trimeric form (ABC). Subunits (B) regulate phosphatase activity and specificity towards the substrate. The existence of multiple forms of PP2A is correlated with the distinct and varied functions of PP2A in vivo.

Recently, different proteins synthesized by pathogens, in particular viral and parasitic proteins, have been implicated in modulating certain specific activities of protein phosphatase 2A.

Different strategies involving PP2A have been adopted by viruses to facilitate their replication and survival in a host cell. As an example, parainfluenza virus incorporates the protein PKCζ, a protein of cellular origin under the control of PP2A, into its viral particle. This can perturb the phosphoylation of host proteins and facilitate its own replication (De B P, Gupta S, Barnejee A K. Cellular protein kinase C ζ regulates human parainfluenza virus type 3 replication. Proc. Natl. Acad Sci USA 1995; 92: 5204-8).

Several DNA viruses with transforming power, such as papovae or adenoviruses, as well as certain retroviruses such as the type 1 human immunodeficiency virus (HIV-1), code for proteins which interact directly with certain host PP2As. All of those viruses comprise proteins which, although structurally different, interact with certain holoenzymes and modify phosphatase activity.

In particular, it has been shown that the E4orf4 protein of adenoviruses binds to a heterotrimeric PP2A and more precisely to a regulating subunit (B), which causes a reduction in the transcription of JunB in the infected cell. That effect could play an important role during viral infection by regulating the apoptotic response of infected cells. Interestingly, it has also been shown that the interaction of E4orf4 with PP2A induces apoptosis in transformed cells in a p53-independent manner (Shtrichman R et al, Adenovirus type 5 E4 open reading frame 4 protein induces apoptosis in transformed cells. J Virol 1998; 72: 2975-82).

Tumor-generating viruses of the Papovae family, including SV40 and polyoma virus, induce cell transformation. It has been shown that PP2A interacts with the "small T" antigen of SV40 or polyoma and with the transforming "middle T" protein of polyoma. Those interactions of viral proteins with PP2A have been clearly involved in viral transformation. Finally, transcriptional regulation, a process normally carried out in the cell by different factors specifically fixing to promoter regulating sequences, probably represents the most important mechanism involved in the control of viral expression by PP2A. It has been demonstrated that PP2A is a negative regulator for numerous transcription factors involved in particular in the processes of cell growth and proliferation, including AP1/SRE, NF-κB, Sp1 and CREB (Waszinski, B E, Wheat W H, Jaspers S, Peruski L F, J R Lickteig R L, Johnson G L, and Klemm D J, Nuclear protein phosphatase 2A dephosphorylates protein kinase A-phosphorylated CREB and regulates CREB transcriptional stimulation. Mol Cell Biol 1993 13, 2822-34). Viral regulation of those transcription factors would permit modulation of viral transcription.

The viral protein of HIV-1, Vpr, interacts in vitro with PP2A and stimulates the catalytic activity of PP2A (Tung L et al, Direct activation of protein phosphatase 2A0 by HIV-1 encoded protein complex Ncp7: vpr. FEBS Lett 1997; 401: 197-201). Vpr can induce the G2 stoppage of infected cells by inhibiting the activation of the p34cdc2-cycline B complex. Further, Vpr interacts with the transcription factor Sp1 and is a weak trans-activator for transcription of Sp1 dependent HIV-1. Thus, the Vpr protein of HIV-1, which is incorporated into the virion, should be involved in vivo in the initiation of viral transcription, a step that is clearly essential for regulating the expression of the Tat transcription factor (a major regulator of transcription encoded by the HIV-1 virus).

In contrast to the well established role of protein kinases in parasitic infections, it is only during the past three years that serine/threonine phosphatases have begun to be recognized as being important potential regulators in the field of parasitology.

Initially, two serine/threonine phosphatases, Ppβ and PfPP, were identified in *Plasmodium falciparum*. The presence of type 1 and type 2A phosphatase activity in the parasite has been demonstrated by enzymological studies. Finally, parasitic enzymes PP2A and PP2B were purified.

Serine/threonine phosphatases have recently been studied in *Theileria parva*, another protozoan close to *P. falciparum*, a cattle parasite. Monocyte and leukocyte host cells infected by the parasite are transformed, resulting in leukemia in the animal. Purified parasites of cells infected with *Theileria* express a protein kinase CK2α. Now, the subunit CK2α should interact with PP2A to positively modulate its activity (HérichéH, et al, Regulation of protein phosphatase 2A by direct interaction with casein kinase 2α. Science 1997; 276: 952-5). Further, modulation of PP2A via expression of the CK2α subunit could be the basis of blockage of two signal routes in the parasitised cell, that of MAP-kinases (Chaussepied M et al. *Theileria* transformation of bovine leukocytes: a parasite model for the study of lymphoproliferation. Res Immunol 1996; 147: 127-38) and that of protein kinase B (Akt) (M Baumgartner, M Chaussepied, M F Moreau, A Garcia, G Langsley. Constitutive PI3-K activity is essential for proliferation, but not survival, of *Theileria parva*—transformed B cells. Cellular Microbiol (2000) 2, 329-339).

The absence of common motifs to the series of proteins interacting with PP2A prevents the informatical identification of peptide motifs directly involved in binding those proteins with PP2A.

Given the major role of protein phosphatase 2As in virus-host interactions or parasite-host interactions as summarized above, the importance of identifying the binding sites of viral or parasitic proteins with PP2A holoenzymes or one of their subunits can be understood, so that novel therapeutic targets for those viral or parasitic pathogens can be identified.

In particular, the identification of peptides interacting with PP2A should allow novel drugs to be developed that can block, by competitive inhibition, the cell mechanisms induced by viral or parasitic proteins via their interaction with PP2A and in particular mechanisms of infection, pathogen proliferation and cell transformation.

SUMMARY OF THE INVENTION

The invention pertains to means for identifying peptides of reduced size, binding a PP2A holoenzyme or one of its subunits. In contrast to native proteins or polypeptide domains of large size, reduced size peptides have the advantage of being readily synthesized, either chemically or in cell systems, in high yields and cheaply. The peptides of the invention are also more stable and more readily transferred into the cytoplasm or into the nucleus of cells using appropriate vectors, with a view to therapeutic use.

DETAILED DESCRIPTION OF THE INVENTION

The invention derives from the demonstration that it is possible to identify peptides with a size of less than 30 amino acids, and in particular peptides less than 20 amino acids in size, interacting with a PP2A holoenzyme or one of its subunits.

In particular, the inventors have shown that using a "SPOT synthesis" technique as described by Frank and Overwing (Methods in Molecular Biology, 1996, vol 66: 149-169, Epitope Mapping Protocols edited by: G E Morris Humana Press Inc, Totowa N.J.) allows binding sites for proteins interacting with a PP2A holoenzyme or one of its subunits to be identified.

As an example, the inventors have identified peptides less than 20 amino acids in size interacting in vitro with purified PP2A holoenzyme or one of its subunits, said peptides being derived from the Vpr protein of HIV-1 or the CK2α protein of the *T parva* parasite. Antagonists derived from these peptides and selected because they inhibit the interaction of viral or parasitic proteins with a particular PP2A holoenzyme could then constitute novel anti-tumoural, antiviral or antiparasitic agents.

The invention concerns a method for identifying a peptide the sequence of which is derived from a viral, parasitic or cellular protein, said peptide specifically binding a type 2A protein phosphatase holoenzyme or one of its subunits, said method comprising the steps consisting of:
  a) depositing, in the form of spots onto a support, peptides the sequence of which is derived from a viral, parasitic or cellular protein, each spot corresponding to the deposit of a peptide with a defined sequence;
  b) bringing the solid support into contact with a solution containing the protein phosphatase 2A holoenzyme or on of its subunits under conditions that allow the peptides present on the support to bind the holoenzyme or one of its subunits; and
  c) identifying on the solid support the peptide to which the protein phosphatase 2A or one of its subunits is bound.

In step a), different peptides are deposited on a solid support in defined positions ("spot"), each position corresponding to a specific peptide sequence and the series then forming a two-dimensional array of peptides. Different methods for preparing such arrays have recently been described (for a review, see Figeys and Pinto, 2001, Electrophoresis 22: 208-216; Walter et al, 2000, Curr Opin Microbiol 3: 298-302). The series of these methods generally include covalently fixing the peptides on a support, in particular using chemical linkers. As an example, the skilled person could refer to the "SPOT synthesis" technique consisting of directly synthesizing peptides comprising up to 20 residues on a cellulose membrane (Frank and Overwing, Methods in Molecular Biology, 1996, vol 66: 149-169, Epitope Mapping Protocols, edited by: G E Morris, Humana Press Inc, Totowa N.J.).

In general, any method can be used provided that it can produce an array of peptides deposited on a solid support that can be used to detect specific interactions between the deposited peptides and particular compounds.

Highly preferably, the series of deposited peptide sequences covers the complete sequence of the viral, parasitic or cellular protein from which those sequences are derived. Thus, the process can test, in a single step, the complete sequence of a given protein, this being "sectioned" into a finite number of peptides with generally overlapping sequences.

In a preferred implementation, the peptides deposited in the form of a spot are less than 20 amino acids in size, and more preferably are less than 15 amino acids in size.

In another particular implementation, the peptides are deposited on a cellulose membrane.

The array obtained is brought into contact in step b) with a type 2A protein phosphatase holoenzyme or one of its subunits.

The term "type 2A protein phosphatase holoenzyme" means any purified dimeric (AC) or heterotrimeric (ABC) complex of a cellular or reconstituted extract after purifying two subunits (A) and (C) of a type 2A protein phosphatase and if necessary a subunit (B). The type 2A protein phosphatases are preferably derived from mammals.

The supports are incubated, for example, in a buffer solution comprising purified protein phosphatase or one of its purified subunits. A suitable buffer solution is TBS (TRIS BORATE) containing 5% of skimmed Régilait (milk) and 3% of BSA.

The peptide onto which the type 2A protein phosphatase holoenzyme is bound is generally identified by direct or indirect labeling of the protein phosphatase and identifying the spots to which the labeled protein has bound. Binding of PP2A or one of its subunits to one of the peptide spots can then be revealed, in particular using antiserums, using techniques that are conventionally used for Western Blot or solid phase ELISA test, after incubating the support containing the peptide array with an antibody directed against subunits (A) or (B) or (C) or a mixture of antibodies directed against subunits (A), (B) or (C) of PP2A.

The method of the invention can be applied to identifying peptides, in particular for use in treating certain viral or parasitic infections, measuring less than 30 amino acids in size or even less than 20 amino acids, said peptides being capable of binding a type 2A protein phosphatase holoenzyme or one of its subunits in vitro.

Further, by using general knowledge in the peptide synthesis field, the skilled person can produce peptides derived from fragments of peptides identified by the method of the invention having the advantageous properties described above.

As a result, the invention provides a natural or synthetic peptide measuring less than 30 amino acids, preferably less than 20 amino acids, characterized in that in vitro, it specifically binds a type 2A protein phosphatase holoenzyme or one of its subunits (A), (B) or (C). The term "specifically binds" means that the peptide is capable of competitively inhibiting binding of a protein of viral or parasitic origin with PP2As.

In a preferred implementation of the invention, the peptide of the invention is characterized in that it is a fragment of a viral, parasitic or cellular protein, said protein binding in vitro a type 2A protein phosphatase or one of its subunits, or a sequence that is distinguished from the preceding protein fragment by substitution or deletion of amino acids, said distinct sequence nevertheless conserving the properties of binding to the type 2A protein phosphatase or one of its subunits. Preferably, the number of amino acids substituted or deleted from the distinct sequence compared with the initial sequence does not exceed 20%, more preferably 10% of the amino acids number constituting the initial sequence. Preferably, only amino acids the deletion of which does not affect the in vitro binding properties of the peptide to PP2A are substituted or deleted.

In particular, one distinct sequence is a peptide sequence increasing the binding affinity to type 2A protein phosphatase or one of its subunits compared with the sequence from which it is derived. A further distinct sequence as defined above is a peptide sequence homologous with an initially identified peptide sequence. The term "homologous peptide" as used in the present invention means a sequence derived from a protein of species other than the initially identified peptide sequence, and for which the primary sequence can be aligned with the peptide sequence initially identified using a conventional optimum alignment program such as the BESTFIT program (Wisconsin Genetics Software Package, Genetics Computer Group, GCG). In particular, a sequence A will be considered to be homologous with a sequence B if said sequences A and B have at least 50% identity, preferably 75% identity after aligning the sequences using an optimum alignment program such as the BESTFIT program. Preferably again, two sequences are also considered to be homologous if the sequences are quasi-identical, with the exception of a few residues that can represent 10% to 20% variability over the whole sequence. Further, amino acids with the same chemical function (such as Arg and Lys) are considered to be equivalent. The peptides to be analyzed for their binding with a PP2A or one of its subunits are generally selected from fragments of viral, parasitic or cellular proteins, which proteins have been shown to interact in vivo or in vitro with a type 2A protein phosphatase.

In particular, such viral parasitic or cellular proteins are selected from one of the following proteins: the t antigen of SV40 or polyoma, the middle t antigen of polyoma, the type B (B, B', B") subunit of PP2A, CK2α, CaMIV, p70S6-kinase, Pak1/Pak3, Tap42/alpha 4, PTPA, Set/I1/I2-PP2A, E4orf4, tau, Vpr or CD28, CCXR2 (chemokine receptor).

A preferred peptide of the invention is a fragment of the CD28 protein, and in particular peptides constituted by the sequences PRRPGPTRKHY (SEQ ID No: 33) and (PRRPGPTRK)$_2$ (SEQ ID No: 34), respectively corresponding to the peptides termed FD2 and FD3 the intracellular penetration capacity and effects on cell viability of which are described below in the experimental section. The present invention also pertains to peptide sequences that are distinguished from the preceding protein by substitution or deletion of amino acids, said distinct sequences nevertheless conserving the properties of binding to type 2A protein phosphatase or one of its subunits.

A particularly preferred peptide of the invention is a fragment of the Vpr protein of the HIV virus, in particular a fragment of the Vpr protein of the HIV-1 or HIV-2 virus, or a sequence that is distinguished from the preceding protein fragment by substitution or deletion of amino acids, said distinct sequence nevertheless conserving the properties of binding to type 2A protein phosphatase or one of its subunits. The invention does not encompass the peptide, a fragment of the Vpr protein having the following sequence: LFIHFRIGC-QHSRIGITRRRRVRDGSSRP* (SEQ ID NO: 44) disclosed in the EMBL database, accession number P89821. In contrast, using said peptide in the context of the applications described below falls within the scope of the present invention.

Special examples of peptides derived from a protein which interacts with type 2A protein phosphatase derived from protamine that can be cited are the peptide with sequence RRRRRRRSRGRRRRTY (SEQ ID No: 41, termed FD8) or a sequence that is distinguished from SEQ ID No: 41 by substitution or deletion of amino acids, said distinct sequence nevertheless conserving the properties of binding to type 2A protein phosphatase or one of its subunits.

Preferably again, a peptide of the invention is characterized in that it is included in one of the following sequences:
  a) VEALIRILQQLLFIHFRI (SEQ ID No: 1);
  b) RHSRIGIIQQRRTRNG (SEQ ID No: 2); or
  c) a sequence that is distinguished from SEQ ID No: 1 or SEQ ID No: 2 by substitution or deletion of amino acids, said distinct sequence nevertheless conserving the properties of binding to type 2A protein phosphatase or one of its subunits.

A particularly preferred peptide of the invention is a fragment of the peptide SEQ ID No: 2, said fragment consisting of or comprising the peptide with sequence RHSRIG (SEQ ID No: 36), termed FD9, the capacity for intracellular penetration and the effect on cell viability of which are described below in the experimental section.

The invention also concerns a compound with a polypeptide framework containing a peptide of the invention as defined above, said compound having a molecular weight in the range 10 to 150 Kdaltons and having the capacity to bind protein phosphatase 2A.

The invention also concerns a polypeptide, characterized in that it is constituted by a repeat of a peptide of the invention.

Particular examples of such polypeptides are the peptide RHSRIG (SEQ ID NO: 36) polymers, and in particular the dimer (RHSRIG)$_2$ (SEQ ID No: 37) or the trimer (RHSRIG)$_3$ (SEQ ID No: 38), respectively termed FD10 and FD11, the capacity for intracellular penetration and the effect on cell viability of which are described below in the experimental section.

Peptides with sequences that are distinguished from SEQ ID No: 1 or SEQ ID No: 2 by substitution or deletion of amino acids and falling within the scope of the invention that can in particular be cited peptides the sequence of which is included in one of the sequences for the Vpr protein of different variants of type HIV-1, HIV-2 and SIV, corresponding to homologous sequences in variants of SEQ ID No: 1 or SEQ ID No: 2.

The following sequences can be cited: VEALIRILQQLL (SEQ ID No: 6), ALIRILQQLLFI (SEQ ID No: 7), IRILQQLLFIHF (SEQ ID No: 8), ILQQLLFIHFRI (SEQ ID No: 9), RHSRIGIIQQRR (SEQ ID No: 10), SRIGIIQQRRTR (SEQ ID No: 11) and IGIIQQRRTRNG (SEQ ID No: 12) corresponding to dodecapeptides identified as binding the subunit A of PP2A.

A particular sequence of the invention that is distinguished from SEQ ID No: 2 by deletion or substitution of amino acids is the sequence RHSRIGVTRQRRARNG (SEQ ID No: 40), also termed FD13 in the experimental section described below.

A preferred peptide of the invention is a peptide selected from sequences SEQ ID No: 1 and SEQ ID No: 2 and is characterized in that its administration induces apoptosis of tumour cells.

One method for selecting peptides that can induce tumour cell apoptosis can be implemented, for example, using the MTT viability test described in the experimental section.

A further preferred implementation of the invention provides a peptide characterized in that it derives from a fragment of the CK2α protein. In particular, the natural or synthetic peptide is characterized in that it derives from a fragment of the CK2α protein of the *Theileria parva* parasite.

More preferably, a peptide of the invention is characterized in that it is included in one of the following sequences:
a) RKIGRGKFSEVFEG (SEQ ID No: 3);
b) TVTKDKCVIKILKPVKKKKIKREIKILQNL (SEQ ID No: 4);
c) KILRLIDWGLAEFYHP (SEQ ID No: 5);
d) a homologous sequence of SEQ ID No: 3, SEQ ID No: 4 or SEQ ID No: 5 derived from *P. falciparum* or *Leishmania*; or
e) a sequence deriving from the sequences mentioned above by substitution or deletion of amino acids, said distinct sequence nevertheless conserving the properties of binding to protein phosphatase 2A or one of its subunits, and in particular the sequence TVTKDCVIKILKPVKKKKIKREIKILQNL (SEQ ID No: 43).

Among peptides that are distinguished from sequences SEQ ID No: 3, 4 or 5 that can be cited are sequences from site 1 (RKIGRGKFSEVFEG) (SEQ ID No: 3), in particular the peptide with the sequence RKIGRGKFSEVF (SEQ ID NO: 31) and the peptide with sequence IGRGKFSEVFEG (SEQ ID NO: 32) or sequences from site 2 (TVTKDKCVIKILKPVKKKKIKREIKILQNL) (SEQ ID No: 4), in particular the following peptides:

```
TVTKDKCVIKIL;      (SEQ ID No: 13)
TKDKCVIKILKP;      (SEQ ID No: 14)
DKCVIKILKPVK;      (SEQ ID No: 15)
CVIKILKPVKKK;      (SEQ ID No: 16)
IKILKPVKKKKI;      (SEQ ID No: 17)
ILKPVKKKKIKR;      (SEQ ID No: 18)
KPVKKKKIKREI;      (SEQ ID No: 19)
VKKKKIKREIKI;      (SEQ ID No: 20)
KKKIKREIKILQ;      (SEQ ID No: 21)
KIKREIKILQNL;      (SEQ ID No: 22)
``` and finally sequences from site 3 KILRLIDWGLAEFYHP (SEQ ID No: 5) or the peptide with sequence KILRLIDWGLAE (SEQ ID No: 23), the peptide with sequence LRLIDWGLAEFY (SEQ ID No: 24), or the peptide with sequence LIDWGLAEFYHP (SEQ ID No: 25).

One example of a peptide of the invention comprising a sequence homologous to *T parva* from site 3 of the CK2α protein in *P falciparum* is the peptide RQKRLI (SEQ ID No: 42). The invention also encompasses polymers of the peptide RQKRLI (SEQ ID NO: 42) and in particular the trimer (RQKRLI)$_3$ (SEQ ID No: 35), termed FD7 in the experimental section.

Preferably, the invention pertains to a peptide derived from the CK2α protein of the parasite *Theileria parva*, characterized in that its administration reduces parasitic development.

A further embodiment of the peptides of the invention is characterized in that the peptides are derived from the tau protein. The tau sequence has a motif corresponding to the binding site for the E4orf4 adenovirus protein. In the case of Alzheimer's disease, the tau protein is regulated by protein phosphatase 2A. Such peptides should thus be useful in treating Alzheimer's disease.

The peptides identified by the method of the invention are particularly useful in treating certain tumours and certain viral or parasitic infections. The skilled person can select, using binding competition tests, novel peptides derived from the sequences identified using the method of the invention, said peptides competitively inhibiting binding of the native protein from which it derives with a holoenzyme PP2A or one of its subunits.

Thus, the invention also concerns a natural or synthetic peptide as defined above, characterized in that it competitively inhibits interaction of the native protein from which it derives with a PP2A holoenzyme or one of its subunits.

In order to be effective in vivo in treating certain tumours or certain viral or parasitic infections, the peptides of the invention can be coupled to a vector that is capable of transferring said peptide into a eukaryotic cell. However, it is possible, as will be discussed below, for the peptides of the invention to themselves have the capacity to penetrate into cells, meaning that the addition of a vector is not required.

Naturally, the invention pertains to means that can synthesise the peptides of the invention. In particular, the invention pertains to a polynucleotide characterized in that its sequence consists of the sequence coding for a peptide of the invention. Preferred polynucleotides are polynucleotides the sequence of which is selected from one of the following sequences:

```
                                        SEQ ID No: 26
(5'GTGGAAGCCTTAATAAGAATTCTGCAACAACTGCTGTTTATTCATTT

CAGAATT);

SEQ ID No: 27
(5'CGACATAGCAGAATAGGCATTATTCAACAGAGGAGAACAAGAAATGG

A);

SEQ ID No: 28
(5'AGGAAGATCGGAAGAGGGAAGTTCAGTGAAGTTTTTGAGGGA);

SEQ ID No: 29
(5'ACAGTAACGAAGGATAAATGCGTAATAAAAATCCTAAAGCCTGTAAA

GAAGAAGAAAATCAAGAGAGAGATTAAGATTCTACAGAACCTA);
or

SEQ ID No: 30
(5'AAAATACTAAGGCTAATTGACTGGGGATTAGCTGAGTTTTACCACCC

A),
respectively coding peptides SEQ ID NOs: 1-5.
```

The invention also concerns polynucleotides with sequences complementary to one of sequences SEQ ID No: 26-30 and sequences hybridizing under stringent conditions to said polynucleotides.

The term "stringent conditions" means conditions that allow specific hybridization of two single strand DNA sequences at about 65° C., for example in a solution of 6×SSC, 0.5% SDS, 5×Denhardt's solution and 100 μg of non specific carrier DNA or any other solution with an equivalent ionic strength and after washing at 65° C., for example in a solution of at most 0.2×SSC and 0.1% SDS or any other solution with an equivalent ionic strength. The parameters defining the stringency conditions depend on the temperature at which 50% of the paired strands separate (Tm). For sequences comprising more than 30 bases, Tm is defined by the relationship: Tm=81.5+0.41 (% G+C)+16.6 log(concentration of cations)−0.63(% formamide)−(600/number of bases). For sequences less than 30 bases long, Tm is defined by the relationship: Tm=4 (G+C)+2(A+T). The stringency conditions have also been defined using protocols described by Sambrook et al, 2001 (Molecular cloning: a laboratory manual, 3$^{rd}$ edition, Cold Spring Harbor, Laboratory Press, Cold Spring Harbour, N.Y.).

It may be advantageous to synthesize a polypeptide comprising a repeat of the peptide motifs identified by the process of the invention. As a result, the invention pertains to a polynucleotide characterized in that it consists of a multimer of a polynucleotide coding for a peptide of the invention. The invention also pertains to a polypeptide characterized in that it is constituted by a repeat of a peptide of the invention.

The invention also pertains to a cell expression vector, characterized in that it comprises a polynucleotide as defined above and regulatory sequences allowing expression of a peptide of the invention in a host cell.

The invention also pertains to a method for preparing a peptide as defined in the invention, comprising transforming a host cell using a cellular expression vector as defined above, followed by culturing the transformed host cell, and recovering the peptide in the culture medium.

The invention further pertains to an antiserum or immunoserum or a purified polyclonal antibody or a monoclonal antibody, characterized in that said antibody or said antiserum or immunoserum is capable of specifically binding a peptide in accordance with the invention.

Antibodies specifically directed against the peptides identified by the process of the invention are obtained, for example, by immunizing an animal after injecting a peptide of the invention, and recovering the antibodies produced. A monoclonal antibody can be obtained using techniques that are known to the skilled person, such as the hybridoma method described by Kohler and Milstein (1975).

The antibodies obtained, specifically directed against targets for protein phosphatase 2A, are of particular application in immunotherapy. As an example, they can act as antagonists for viral or parasitic proteins directed against protein phosphatase 2A to block viral or parasitic development.

Similarly, polynucleotides encoding the peptides of the invention can be directly transferred to the nucleus of target cells, if necessary using suitable vectors, to allow in vivo expression of the corresponding peptides, said peptides being susceptible of blocking by competitive inhibition a specific interaction between the protein phosphatase 2A and the viral or parasitic protein from which they derive.

The invention thus pertains to a pharmaceutical composition comprising one of the elements selected from a polynucleotide of the invention or an antibody of the invention.

The invention also concerns a pharmaceutical composition comprising one of the peptides of the invention in combination with a pharmaceutically acceptable vehicle.

The invention further concerns the use of a peptide of the invention as defined above in preparing a drug for use in treating a viral or parasitic infection.

Preferably, the invention concerns the use of a peptide the sequence of which derives from a fragment of the Vpr protein as defined above, in preparing a drug that can inhibit an HIV infection.

The peptides of the invention can advantageously be selected so as to stimulate the induction of apoptosis linked to activation of cellular protein phosphatase 2A. Thus, the invention also concerns the use of a peptide of the invention as defined above in preparing a drug that can induce apoptosis of target cells and in particular tumour cells.

In a further preferred aspect, the invention concerns the use of a peptide the sequence of which derives from a fragment of the CK2α protein in preparing a drug that can inhibit parasitic infection. More particularly, the invention concerns the use of a peptide in preparing a drug for use in treating malaria.

The viral or parasitic infection results in specific expression of proteins comprising sequences of peptides of the invention. The sequences encoding the peptides of the invention can thus be used as a probe to detect, in a specific manner from RNA extracted from a biological sample from a patient, a specific viral infection or parasitic infection.

Similarly, an antibody of the invention can be used to specifically recognize peptide sequences contained in viral or parasitic proteins expressed during infection.

Thus, the invention concerns the use of a polynucleotide of the invention or an antibody of the invention in the in vitro diagnosis of parasitic or viral diseases.

The invention also pertains to the selection and use of a peptide binding protein phosphatase 2A, and capable of penetrating into cells.

An example of such a peptide is illustrated by the peptide FD6 (SEQ ID No: 20) derived from the CK2α protein of *T. parva*. It has been shown in the present invention that the presence of that peptide in the cell does not affect the viability of cultivated or maintained mammal cells alive.

The experimental section below illustrates an application of the method for identifying the peptides of the invention to identifying peptides from the Vpr protein of HIV-1 and of the CK2α protein from the *Theileria parva* parasite. The invention also pertains to the selection and use of a peptide binding protein phosphatase 2A and possibly capable of penetrating into a cell, said peptide enabling targeting of and contact with intracellular protein phosphatase 2A of a molecule capable of regulating the activity of protein phosphatase 2A.

BRIEF DESCRIPTION OF THE FIGURES

FIG. 1: Screening of a membrane containing peptides covering the sequence for Vpr of HIV-1 with the structural subunit A of PP2A (A) and the holoenzyme PP2A1 (B).

Covering the sequence of four peptides 54-57 defines the sequence of site 2 VEALIRILQQLLFIHFRI (SEQ ID No: 1)

| Peptide 54: | VEALIRILQQLL | (SEQ ID NO: 6) |
| Peptide 55: | ALIRILQQLLFI | (SEQ ID NO: 7) |
| Peptide 56: | IRILQQLLFIHF | (SEQ ID NO: 8) |
| Peptide 57: | ILQQLLFIHFRI | (SEQ ID NO: 9) |

Covering the sequence of three peptides 64 to 66 defines the sequence of site 1 RHSRIGIIQQRRTRNG (SEQ ID No: 2)

| Peptide 64: | RHSRIGIIQQRR | (SEQ ID NO: 10) |
| Peptide 65: | SRIGIIQQRRTR | (SEQ ID NO: 11) |
| Peptide 66: | IGIIQQRRTRNG | (SEQ ID NO: 12) |

FIG. 2: Screening of a membrane containing peptides covering the sequence for CK2α of *Theileria* with (A) the structural subunit A of PP2A and (B) the holoenzyme PP2A1.

Covering the sequence of two peptides defines the sequence of site 1 RKIGRGKFSEVFEG (SEQ ID No: 3)

| Peptide 66: | RKIGRGKFSEVF | (SEQ ID NO: 31) |
| Peptide 67: | IGRGKFSEVFEG | (SEQ ID NO: 32) |

Covering the sequence of ten peptides 74-83 defines the sequence of site 2 TVTKDKCVIKILKPVKKK-KIKREIKILQNL (SEQ ID No: 4).

| Peptide 74: | TVTKDKCVIKIL | (SEQ ID NO: 13) |
| Peptide 75: | TKDKCVIKILKP | (SEQ ID NO: 14) |
| Peptide 76: | DKCVIKILKPVK | (SEQ ID NO: 15) |
| Peptide 77: | CVIKILKPVKKK | (SEQ ID NO: 16) |
| Peptide 78: | IKILKPVKKKKI | (SEQ ID NO: 17) |
| Peptide 79: | ILKPVKKKKIKR | (SEQ ID NO: 18) |
| Peptide 80: | KPVKKKKIKREI | (SEQ ID NO: 19) |
| Peptide 81: | VKKKKIKREIKI | (SEQ ID NO: 20) |
| Peptide 82: | KKKIKREIKILQ | (SEQ ID NO: 21) |
| Peptide 83: | KIKREIKILQNL | (SEQ ID NO: 22) |

Covering the sequence of three peptides defines the sequence of site 3 KILRLIDWGLAEFYHP (SEQ ID No: 5)

| Peptide 129: | KILRLIDWGLAE | (SEQ ID NO: 23) |
| Peptide 130: | LRLIDWGLAEFY | (SEQ ID NO: 24) |
| Peptide 131: | LIDWGLAEFYHP | (SEQ ID NO: 25) |

Figure 3:
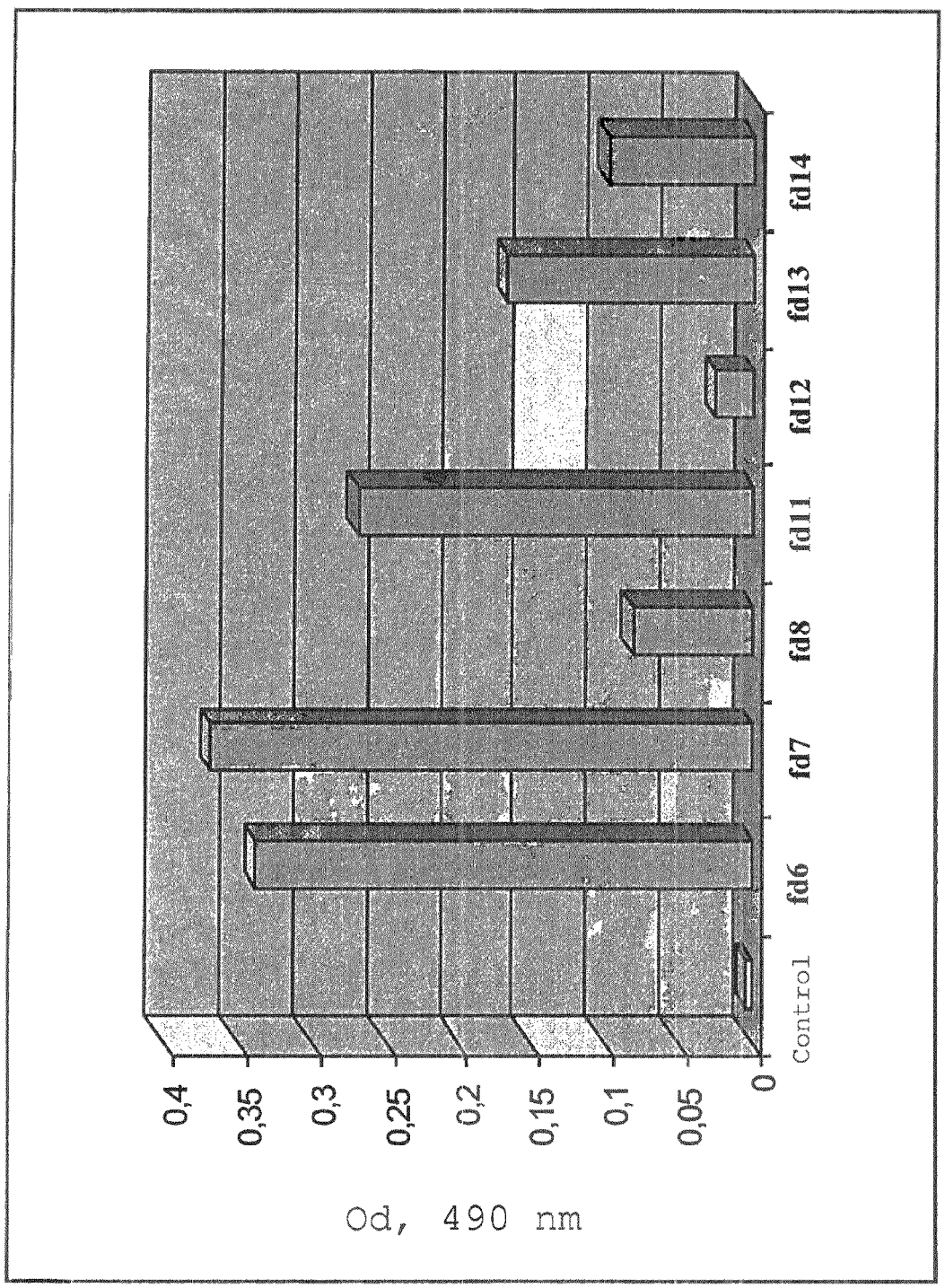

FIG. 3: is a histogram representing the intracellular penetration values obtained using a cell penetration test for the peptides cited in Table 3.

Figure 4A:
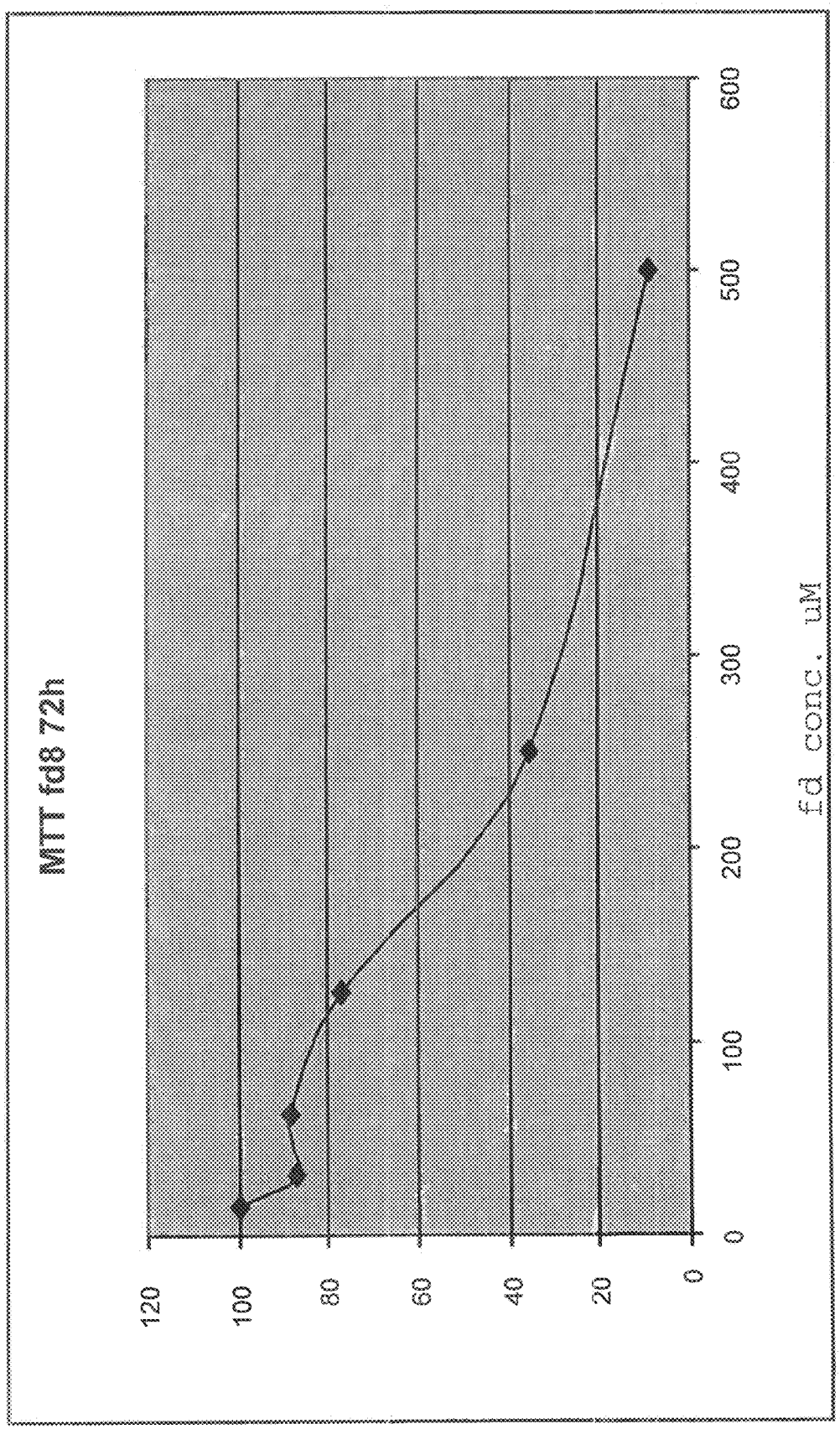
Figure 4B:
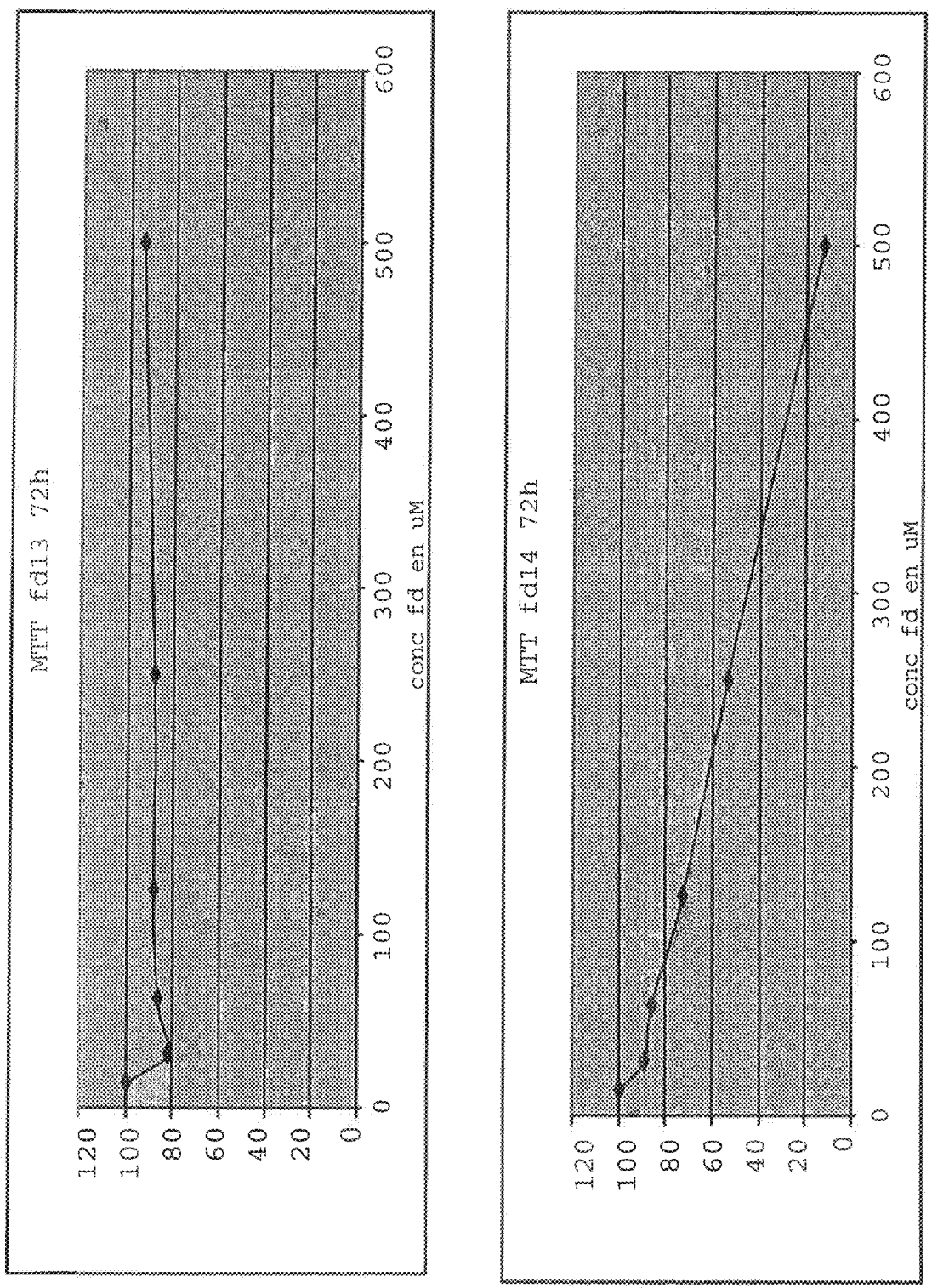
Figure 4C:
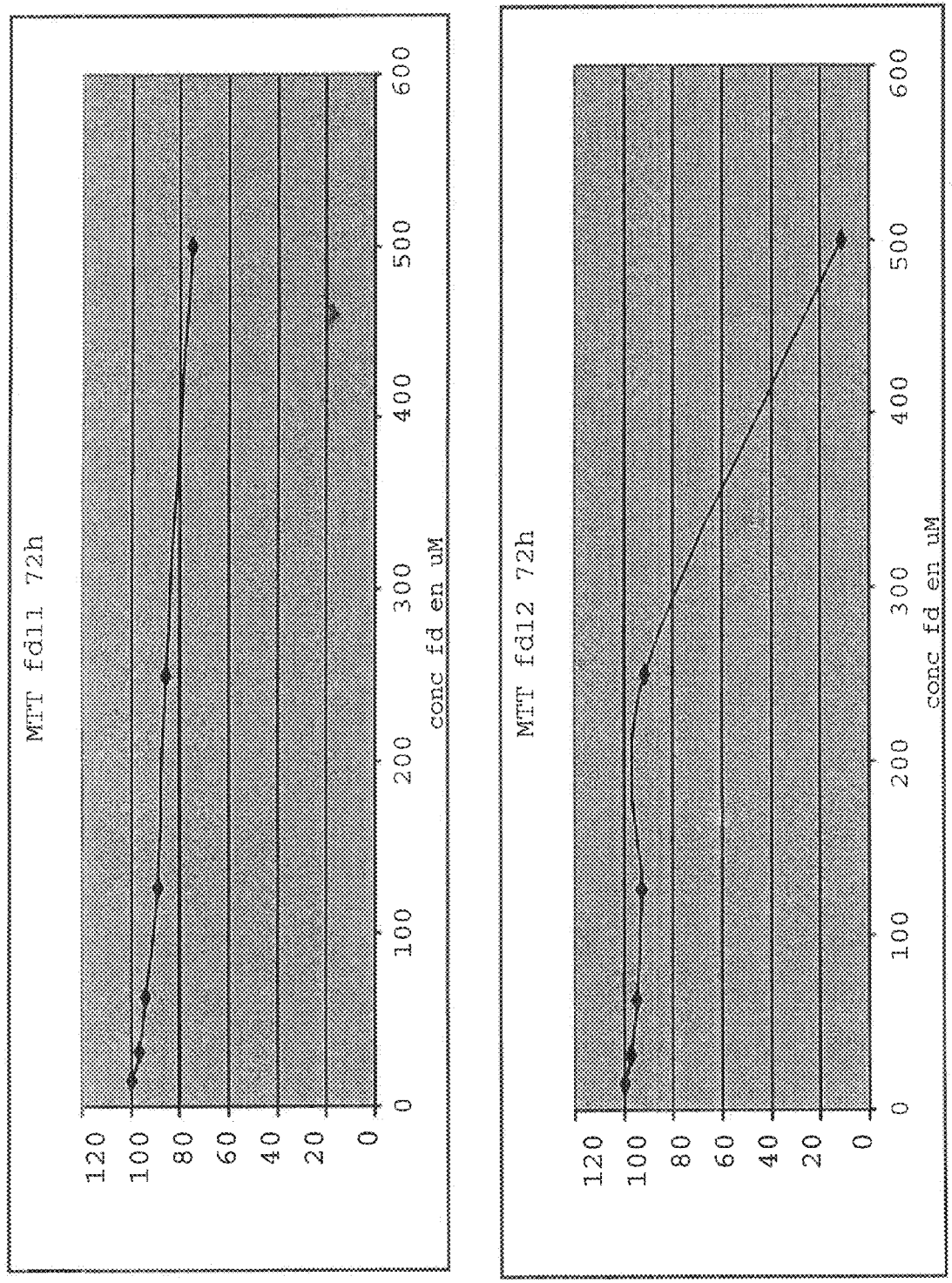

FIG. 4: illustrates the effects of different peptides on the viability of Hela cells evaluated using a MTT viability test.

The viability of Hela cells (expressed as a percentage with respect to the initial population) was tested in the presence of increasing concentrations of peptides FD8 (4A), FD13/FD14 (4B) and FD11/FD12 (4C).

EXAMPLES

A. Materials and Methods

A.1. Purified PP2A Proteins

Trimeric PP2A1 protein was purified to homogeneity from pig brain.

A recombinant structural subunit of PP2A was expressed in *E. coli* and purified using the protocol described by Cohen et al (Cohen P, Alemany S, Hemmings B A, Resink T J, Stralfors P, Tung H Y. Protein phosphatase-1 and protein phosphatase 2A from rabbit skeletal muscle. Methods Enzymol 1988 159, 390-408), or that described by Bosch et al (Bosch M, Cayla X, Van Hoof C, Hemmings B A, Ozon R, Merlevede W, Goris J. the PR55 and PR65 subunits of protein phosphatase 2A from Xenopus laevis. Molecular cloning and developmental regulation of expression. Eur J Biochem 1995, 230, 1037-45).

A.2. Method for Identifying HIV Vpr Binding Sites and *Theileria parva* (*T parva*) Ck2α Binding Sites with PP2A Binding peptides derived from CK2α proteins (encoded by *T parva* protozoa) or Vpr protein (encoded by the HIV-1 virus) with PP2A were identified using the "spot peptides" technique described above (Frank and Overwing, 1996, Meth Mol Biol 66, 149-169).

The method consisted of synthesizing dodecapeptides, in situ on a cellulose membrane, at defined positions wherein the series of the sequence covered the whole sequence of the protein of interest (Vpr or CK2α). The peptides of two consecutive spots on the membrane overlap with an overlapped by two amino acids.

Sixty-eight (68) dodecapeptides covering the whole sequence of the Vpr protein of HIV-1 and two hundred and five (205) dodecapeptides covering the sequence for the CK2α protein of *Theileria* were synthesized and covalently bound to cellulose membranes.

Figure 2A:
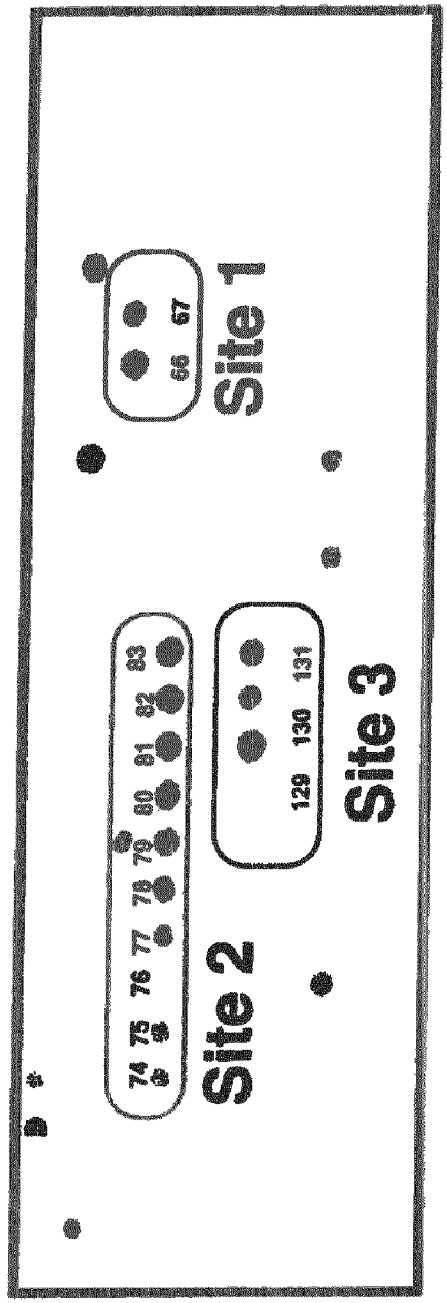
Figure 2B:
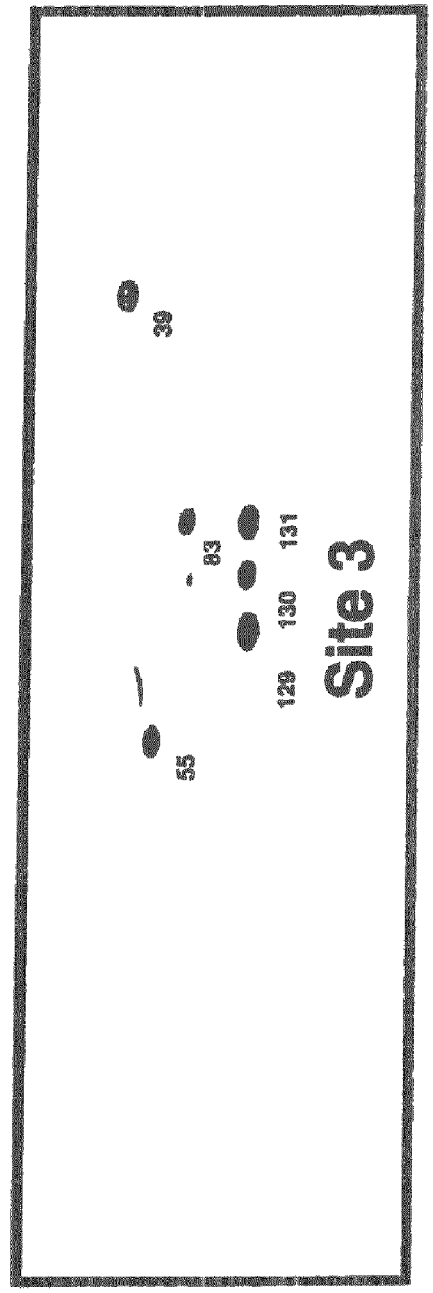

Each prepared membrane was first saturated for 1 hour at ambient temperature with TBS containing 5% skimmed Régilait (milk) and 3% BSA then incubated overnight in the same buffer in the presence of 4 µg/ml of purified protein (subunit A of PP2A or holoenzyme PP2A1). The specific interaction of each purified protein (respectively the structural subunit A or the trimeric holoenzyme PP2A1) with a peptide sequence was revealed, as in Western blot, after incubating the membrane with an antibody directed against the structural protein A (FIGS. 1A and 2A) and with a mixture of antibodies recognizing the proteins A, B and C of PP2A (FIGS. 1B and 2B).

The membranes were washed 5 times for 15 minutes with a conventional TBST buffer (TBS+TWEEN) used for incubation then incubated a further 1 hour at ambient temperature with a second antibody (coupled with peroxidase). Finally, the membranes were washed 5 times for 15 minutes with the TBST buffer and revealed.

A.3. Cell Penetration Test

1—Cells

We analyzed the Hela line, which is derived from a human cervical carcinoma.

2—Quantitative Determinations of Internalized Peptides

Lysis Buffer 0.1 M Tris buffer, pH 8 containing 0.5% NP40.

OPD Buffer 25.7 ml of 0.2 M dibasic sodium phosphate+24.3 ml of 0.1 M citric acid+50 ml distilled water; adjust to pH 5.0.

Biotinylated-Avidine Peptide Complexes 4 moles of peptides were incubated with 1 mole of avidine-peroxidase. 20 minutes at ambient temperature.

Analysis of Intracellular Penetration of Various Peptides into Hela Cell

Hela cells ($10^4$ in 100 l) were seeded into 96-well plates (flat bases) with complete DMEM medium in the presence of 2.5% penicillin/ampicillin and 10% foetal calf serum. After incubating overnight at 37° C. in a $CO_2$ oven (5%), different dilutions of complexes (biotinylated-avidine peroxidase peptides) were added. After incubating for 4 hours the supernatant was aspirated and the cells were washed 3 times with PBS, trypsinated and taken up for counting in PBS. After counting, the cells were taken up in 300 μl of lysis buffer.

Measurement of Peroxidase Activity

50 μl of OPD buffer was incubated in a 96 well ELISA plate with 50 μl of lysis buffer or 50 μl of cell lysate (in general, different successive dilutions were carried out (to ½)). In order to reveal, 50 μl of OPD solution was added (in the dark). The reaction (about 10 min) was stopped with 100 μl of 1N HCl.

Analysis of Results

The peroxidase activity was determined by reading at 490 nm in the ELISA reader (reference filter at 620 nm) and the quantity of peroxidase in the lysates was calculated from the calibration curve then extrapolated to the same number of cells ($10^3$ or $10^4$):

Peptide molecules=$(6*10^{23}/MW$ of peptide)*ng of $PO*10^{-9}$.

A.4. Cell Viability Test

Hela cells ($10^4$ for 100 μl) were seeded into 96-well plates (flat bases) with complete DMEM medium containing 2.5% penicillin/ampicillin and 10% foetal calf serum. After incubating overnight at 37° C. in a $CO_2$ oven (5%), the cells were cultivated in the presence of different peptide concentrations. After incubating for 72 h, the medium containing the peptides was aspirated and the MTT at 0.5 mg/ml (diluted in DMEM alone) was added in an amount of 100 μl per well. Incubation was carried out in the dark at 37° C. for 30 minutes then the MTT was aspirated off and 50 μl of DMSO was added to all wells. It was necessary to wait ten minutes for complete lysis of the cells and to agitate the lysate well to homogenize dissolution of the reaction product in the wells. The plates were then read at 570 nm with a 690 nm reference filter.

B. Results and Discussion

B.1. Identification of Peptide Sequences Containing Binding Sites for Proteins Coded by Two Pathogenic Agents (HIV-1 and *T. parva*) with PP2A (PP2A1 and Subunit A)

The results obtained after incubating membranes containing peptides covering the sequences for Vpr of HIV-1 and CK2α of *T parva* with purified trimeric PP2A holoenzyme allowed five sequences of Vpr and CK2α peptides to be determined that were capable of specifically binding PP2A and are shown in the table below:

TABLE 1

Peptide sequences containing binding sites for HIV-1 Vpr and CK2α with PP2As

| | | subunit A | PP2A1 |
|---|---|---|---|
| HIV-1 Vpr | site 1 | RHSRIGIIQQRRTRNG (SEQ ID NO: 2) | RHSRIGIIQQRRTRNG (SEQ ID NO: 2) |
| | site 2 | VEALIRILQQLLFIHFRI (SEQ ID NO: 1) | |
| T parva CK2α | site 1 | RKIGRGKFSEVFEG (SEQ ID NO: 3) | |
| | site 2 | TVTKDKCVIKILKPVKKKKIKREIKILQNL (SEQ ID NO: 4) | |
| | site 3 | KILRLIDWGLAEFYHP (SEQ ID NO: 5) | KILRLIDWGLAEFYHP (SEQ ID NO: 5) |

More precisely, two peptide sequences containing a binding site for the Vpr of HIV-1 with the protein PP2A1 (FIG. 1B, "site 1") and with the subunit A (FIG. 1A, "site 1" and "site 2") were identified. Three peptide sequences containing a binding site for CK2α of *T parva* with the protein PP2A1 (FIG. 2B, "site 3") and with the structural subunit A were also identified (FIG. 2A, "site 1", "site 2" and "site 3").

B.2. Importance of Using HIV-1 Vpr Peptides which Bind PP2A

The exogenic expression or expression due to proviral infection of the Vpr of HIV-1 induces apoptosis in Hela cells, T lymphoid lines and primary lymphocytes (Stewart et al, 1997 J Virol 71: 5579-9). The use of Vpr mutants initially allowed this effect to be correlated with stopping cells in phase G2 of the cell cycle. More recently, it has been shown that Vpr can also induce apoptosis independently of stopping at G2 (Nishizawa et al, 2000, Virology 27, 16-26).

It has been reported that activation of PP2A after interaction with the E4orf4 adenoviral protein induces apoptosis in transformed cells (Shtrichman R et al, 2000, Oncogene 19, 3757-3765). Analogously, expression of Vpr also induces apoptosis in transformed cells (Stewart et al, 1999, PNAS, 96, 12039-12043).

Further, an analysis of Vpr mutants known in the art indicates that the peptides identified by the process of the invention and specifically binding the PP2A protein contain sequences which correlate with those required for the pro-apoptotic effect of Vpr.

Thus, fragments of viral proteins, Vpr and E4orf4, which interact with PP2A and are identified by the process of the invention, could be useful in inducing apoptosis of tumor cells.

The identified peptides are also naturally used in inhibiting infection by HIV or other related viruses and retroviruses.

B.3. Importance of Using *T parva* Ck2α Sequences that Bind PP2A

The use of okadaic acid and the small t antigen of SV40 has demonstrated that PP2A controls cell proliferation via a novel cascade of phosphorylations involving PI3-kinase, PKCζ (identified as a MAP-kinase-kinase-kinase or MEKK), the MEK protein and the two MAP kinases ERK-1 and ERk-2, and transcription factors NF-κB and Sp1 (Sontag E, Sontag J M, Garcia A (1997), EMBO J, 16, 5662-5671; Ayllon V, Martinez A, C, Garcia A, Cayla X and Rebollo A (2000), EMBO J. 19, 1-10, A Garcia, S Cereghini, E Sontag (2000), J Biol Chem 275, 9385-9389). Further, the role of PP2A in regulating the cascade of MAP kinases has also been suggested by studies by Chambaz's team (Hériché et al, (1997), Science, 276, 952-955) which have shown that overexpression of the cellular CK2α subunit activates PP2A which dephosphorylates the MEK protein.

Studies by Ole-Moi et al (Embo J, 1993, 12, 1621-1631) have shown that transformation by *Theileria* induces hyperphosphorylation of host proteins. This effect is partially due to constitutive activation of cellular CK2 which should itself depend on the action of a CK2α type subunit coded by the parasite and secreted into the cytosol of the transformed cell.

As indicated below, a comparison of the sequences identified by the process of the invention corresponding to the three binding sites with PP2A allows the presence of a motif of the type: K-I-G/L-R/K, which is partially repeated in site 2, to be identified.

```
Site 1: KIGR                      (SEQ ID NO: 45)

Site 2: KILKPVKKKKIKREKILQNL      (SEQ ID NO: 46)

Site 3: KILRLI                    (SEQ ID NO: 47)

(partial duplication, KIL/RLI).
```

It is interesting to note that the binding site for the ATP of CK2α partially covers site 1 and site 2, which suggests inhibition of kinase activity after interaction of CK2α with the subunit A. Further, as will be seen from Table 2 below, the three sequences containing the binding sites for CK2α of *T parva* with PP2A are conserved among a number of species including *P. Falciparum* and *Leishmania* parasites.

TABLE 2: Comparison of various sequences of CK2α with peptides from *T. parva* containing binding sites with PP2A (the sequences of *P. falciparum* are deduced from an EST; the others are from the "Swissprot" gene bank). Only residues that differ from the *T. parva* sequence are indicated.

Site 1

```
                                            (SEQ ID NO: 3)
    T.parva/Leishmania      R KIGRGKFSEV FEG
```

*Pfalciparum*/Bovine/Dictyo Y

Site 2

```
                                            (SEQ ID NO: 4)
T.parva
TVTK D K C VIKI LKPVKKKKIKREIKI LQNL (SEQ ID NO: 48)
Pfalciparum
ECN R P A V
```

-continued

```
                                            (SEQ ID NO: 49)
Bovine
N N- E V E (SEQ ID NO: 50)
Leishmania
NN E KV V V E (SEQ ID NO: 51)
Leishmania
KVL R Q V -L MV T
```

Dictyo

Site 3

```
T.parva    K I L RLIDWGLAEFYH P    (SEQ ID NO: 5)
```

*Leishmania* G K I

*Pfalciparum* R Q K

Bovine R K

A careful analysis of the interactions suggests that the CK2α from these different species should interact with PP2A; as an example peptide 131 from *T parva* CK2α described in FIG. 2 and in which the first four amino acids of site 3 are deleted is capable of binding PP2A. This suggests that the CK2α of *Leishmania, P falciparum*, which differ in their 3 first amino acids, should bind PP2A. This is consistent with the fact that the KILRLI (SEQ ID NO: 47) motif has a duplication of K/R-II/L-I/L which, in a basic context, could be a binding site for PP2A.

The presence inside the cell of these peptides, corresponding to the in vivo binding sites of proteins with PP2A, could thus interfere with the development of those parasites.

B. 4. Biological Effects of Peptide Compounds of the Invention on Cells

The various peptides listed in Table 3 were synthesized in the biotinylated form, purified by HPLC (Neosystem) and their effect on intracellular penetration and cell viability was analyzed in Hela cells. A study of the series of peptides shown in Table 1 has allowed six peptides to be determined which have the possibility of penetrating into the Hela cell (FIG. 3).

- FD6: a 12AA peptide derived from a site for interaction of the A subunit of PP2A with the *T parva* CK2α protein;
- FD7: a 18AA peptide corresponding to three repeats of a 6AA hexa motif; this sequence, derived from *P falciparum* CK2α, is homologous with the *T parva* sequence that binds PP2A;
- FD8: a peptide derived from protamine (a known PP2A activator);
- FD11: a 18AA peptide corresponding to three repeats of a 6AA hexa motif derived from the sequence for FD14;
- FD14: FD14, which reproduces the binding site which we have characterized from HIV-1 Vpr with PP2A;
- FD13: This peptide corresponds to a HIV-1 Vpr sequence which is homologous with the FD14 peptide sequence, which represents a binding site with PP2A with another HIV-1 Vpr.

Further, viability studies carried out on the series of peptides shown in Table 1 allowed three peptides to be identified which inhibit the viability of Hela cells:

- FD8: affects the viability of Hela cells (FIG. 4A);
- FD14: clearly affects the viability of Hela cells (FIG. 4B);
- FD12: a 18AA peptide the sequence of which derives from that of the FD11 peptide (R is mutated into A). This peptide, which is homologous with the glucosamine transferase protein of *Chlamydia muridarum*, affects the viability of the Hela cell (FIG. 4C). This biological effect could be due to an interaction with the plasma membrane.

TABLE 3

Peptides mimicking binding sites for target proteins with PP2As

| Original proteins | peptide codes | peptide sequences | SEQ ID No: |
|---|---|---|---|
| CD28 | FD2 | -PRRPGPTRKHY | SEQ ID No: 33 |
|  | FD3 | -(PRRPGPTRK)2 | SEQ ID No: 34 |
| CK2α T parva | FD6 | -VKKKKIKREIKI | SEQ ID No: 20 |
| CK2α P. Falciparum (T parva analogue) | FD7 | -(RQKRLI)3 | SEQ ID No: 35 |
| Vpr (HIV-1) | FD9 | -RHSRIG | SEQ ID No: 36 |
|  | FD10 | -(RHSRIG)2 | SEQ ID No: 37 |
|  | FD11 | -(RHSRIG)3 | SEQ ID No: 38 |
|  | FD12* | -(AHSRIG)3 (FD11 mutation, R . . . A) | SEQ ID No: 39 |
|  | FD13 | RHSRIGVTRQRRARNG (FD14 analogue) | SEQ ID No: 40 |
|  | FD14 | RHSRIGIIQQRRTRNG | SEQ ID No: 2 |
| Protamine | FD8 | RRRRRRRSRGRRRRTY | SEQ ID No: 41 |

DISCUSSION

Are peptides from certain proteins which interact with PP2As a novel anti-tumoral approach?

Our study has allowed to identify two penetrating peptides (FD8/FD14) derived from two proteins, Vpr and protamine, known to interact with PP2As. These peptides, which have in common sequences rich in arginine and lysine, could thus penetrate into the cell using a general internalization mechanism. Such a mechanism, which is common in internalizing peptides having arginine-rich sequences, has recently been proposed (Tomoki Suzuki et al, 2002, Possible existence of common internalization mechanisms among arginine-rich peptides, JBC 277, 2437-2443). In general, the presence of sequences that are rich in arginine or lysine characterize proteins binding PP2As, which suggests that other penetrating peptides could be identified in the PP2A family.

Vpr, a protein coded by the HIV-1 virus, is involved in maintaining a high viral charge and in establishing pathogenesis linked to HIV. The expression of Vpr, exogenic or due to proviral HIV-1 infection, induces apoptosis in Hela cells, in T lymphoid lines, in primary lymphocytes and in transformed cells (Stewart et al, J Virol 1997, 71, 5579-9; Stewart et al 1999, PNAS, 96, 12039-12043). Further, it has been reported that the interaction of PP2A with a further viral protein, adenovirus E4orf4 (Marcellus et al, J Virol 2000, 74, 7869-7877) can induce apoptosis in tumor cells. In total, these results suggest the hypothesis that activation of certain PP2As would be a novel means of inducing tumor apoptosis. In this regard, our results shown in FIG. 4B suggest that the F14 peptide derived from HIV-1 Vpr could represent an anti-tumoral biopeptide. The absence of the biological effect of peptide FD13 (the sequence for which differs by four AA compared with FD14—see Table 2) suggests that the structure of FD14 is critical in regulating Hela viability. As a result, the production of chemical molecules mimicking the structure of the FD14 peptide could thus allow novel anti-tumoral substances to be generated.

---

The invention claimed is:

1. A peptide, which specifically binds a type 2A protein phosphatase holoenzyme or one of its subunits in vitro, which is a fragment of the CK2α protein, and which consists of a sequence selected from the group consisting of:

```
    IKILKPVKKKI;      (SEQ ID No: 17)
    ILKPVKKKKIKR;     (SEQ ID No: 18)
    KPVKKKKIKREI;     (SEQ ID No: 19)
    VKKKKIKREIKI;     (SEQ ID No: 20)
    KKKIKREIKILQ;     (SEQ ID No: 21)
    KIKREIKILQNL;     (SEQ ID No: 22)
``` and an isolated peptide which differs from SEQ ID NOS: 17-22 only by substitution or deletion of one or more amino acids, wherein the isolated peptide consists of a sequence having 80% or higher homology to any peptide of SEQ ID NOS: 17-22, and wherein the isolated peptide conserves the property of binding to the type 2A protein phosphatase holoenzyme or one of its subunits in vitro.

2. The peptide according to claim 1, which consists of IKILKPVKKKI (SEQ ID NO: 17).

3. The peptide according to claim 1, which consists of ILKPVKKKKIKR (SEQ ID NO: 18).

4. The peptide according to claim 1, which consists of KPVKKKKIKREI (SEQ ID NO: 19).

5. The peptide according to claim 1, which consists of VKKKKIKREIKI (SEQ ID NO: 20).

6. The peptide according to claim 1, which consists of KKKIKREIKILQ (SEQ ID NO: 21).

7. The peptide according to claim 1, which consists of KIKREIKILQNL (SEQ ID NO: 22).

8. The peptide according to claim 1, which consists of the isolated peptide which differs from SEQ ID NOS: 17-22 only by substitution or deletion of one or more amino acids, wherein the isolated peptide consists of a sequence having 80% or higher homology to any peptide of SEQ ID NOS: 17-22, and wherein the isolated peptide conserves the property of binding to the type 2A protein phosphatase holoenzyme or one of its subunits in vitro.

9. The peptide according to claim 1, which consists of the isolated peptide which differs from SEQ ID NOS: 17-22 only by substitution or deletion of one or more amino acids, wherein the isolated peptide consists of a sequence having 90% or higher homology to any peptide of SEQ ID NOS: 17-22, and wherein the isolated peptide conserves the property of binding to the type 2A protein phosphatase holoenzyme or one of its subunits in vitro.

* * * * *